Figure 1:
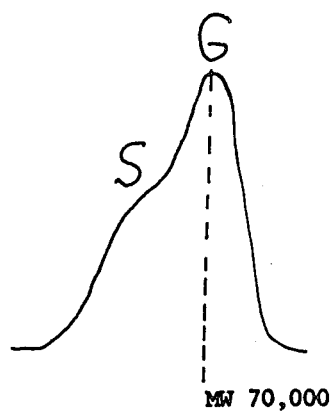

United States Patent [19]

Bonhard et al.

[11] 4,336,248

[45] Jun. 22, 1982

[54] PREPARATION OF COUPLED HEMOGLOBIN MOLECULES

[75] Inventors: Klaus Bonhard, Hanau; Uwe Boysen, Frankfurt, both of Fed. Rep. of Germany

[73] Assignee: Biotest-Serum-Institut GmbH, Frankfurt am Main, Fed. Rep. of Germany

[21] Appl. No.: 624,220

[22] Filed: Oct. 20, 1975

[30] Foreign Application Priority Data

Oct. 21, 1974 [DE] Fed. Rep. of Germany ....... 2449885

[51] Int. Cl.³ .................. A61K 35/14; C07G 7/00; C07C 103/52; A61K 37/00
[52] U.S. Cl. .................. 424/101; 260/112 B; 260/112.5 R; 424/177
[58] Field of Search ............ 260/112 B, 112.5 R; 424/177

[56] References Cited

U.S. PATENT DOCUMENTS 3,925,344 12/1975 Mazur .................. 424/177
4,001,200 1/1977 Bonsen et al. .......... 260/112 B
4,009,267 2/1977 Huber et al. ........... 260/112 B

OTHER PUBLICATIONS

Rabiner et al., *J. Expl. Med.*, vol. 126, (1967), pp. 1127–1142.
Ciba-Geigy, *Documents, Scientific Tables*, (1973), p. 597.
Savitsky et al., *Clin. Pharmacol. Ther.*, Jan. 1978, pp. 73–80.
Wold, Methods in Enzymology, XI, 617–618, 638–639 (1967).
Fasold et al., Angew. Chem. Internat. Ed., 10, 795–801 (1971).

*Primary Examiner*—Delbert R. Phillips

[57] ABSTRACT

Hemoglobin molecules are coupled so as to increase their intravascular residence times without significantly diminishing their oxygen transport ability. This is achieved by coupling hemoglobin molecules to one another and/or to serum proteins and gelatin derivatives using dialdehydes such as aliphatic dialdehydes of 3 to 8 carbon atoms, optionally followed by addition of pyridoxal phosphate. The desired material isolated by ammonium sulfate precipitation, the sulfate being added before, simultaneously with, or after the dialdehyde. Solution of the precipitate followed by dialysis and/or ion exchange can also be undertaken.

12 Claims, 18 Drawing Figures

Profile I      Profile II      Profile III

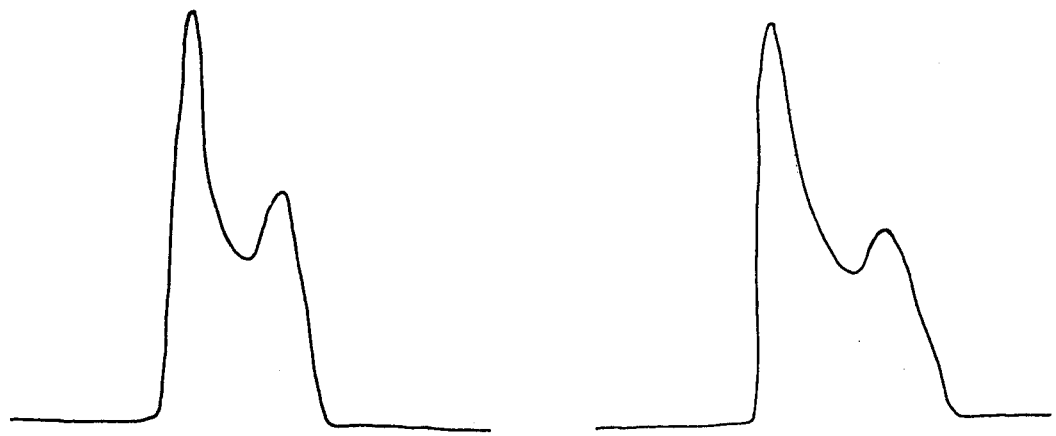
Fig. 11
Fig. 12
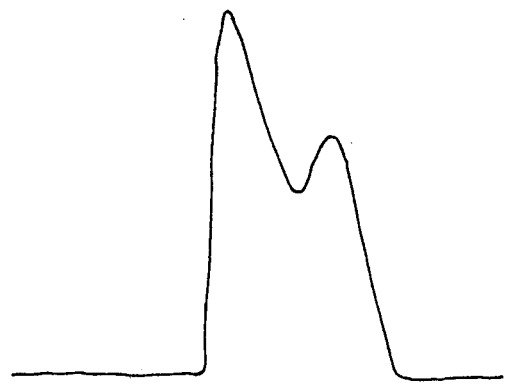
Fig. 13
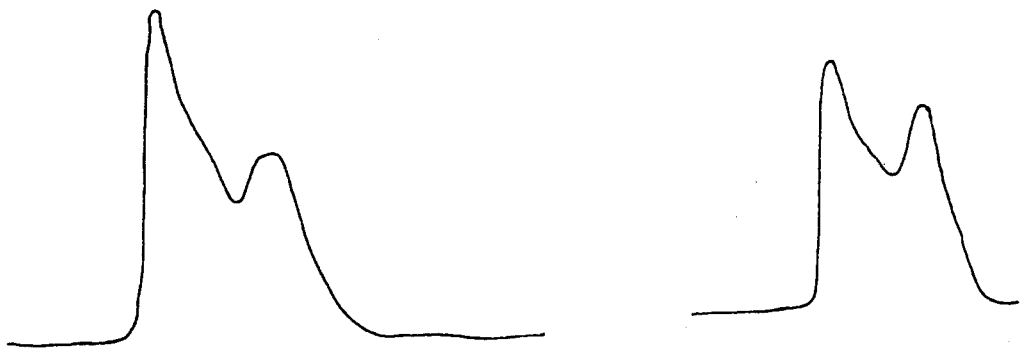
Fig. 14
Fig. 15

PREPARATION OF COUPLED HEMOGLOBIN MOLECULES

The present invention relates to improved hemoglobin-containing preparations.

For acute blood replacement and organ perfusion, it is known that stroma-free solutions of human hemoglobin container physiological electrolyte can be applied intravenously to obtain an increased transport of oxygen (Compare, for instance, S. F. Rabiner et al; J. Ex. Med. 126, 1127–1142 [1967]). In practice, however, it is desired to achieve a longer residence time of the molecules transporting oxygen for a longer-lasting intravascular effect than has heretofore been achieved. Increasing the particle size of the oxygen carriers by chemical coupling to each other or to other molecules has heretofore always resulted in loss of the physiological oxygen bonding property (H. Fasold et al., Angewandte Chemie 83, 875–882 [1971]).

It is accordingly an object of the present invention to provide preparations exhibiting the oxygen transport properties of hemoglobin along with increased intravascular residence times.

These and other objects are realized in accordance with the present invention pursuant to which hemoglobin molecules are coupled to one another and/or other proteins such as serum proteins and gelatin derivatives.

This coupling is effected by starting with substantially oxygen-free hemoglobin, i.e., in the known desoxy form, and reacting it with a dialdehyde, optionally in the presence of other proteins. The dialdehyde advantageously is an aliphatic dialdehyde of 3 to 8 carbon atoms. The coupled product is advantageously salted out with ammonium sulfate added to the hemoglobin preparation before, simultaneously with or after the dialdehyde. The precipitate can then be dissolved in water, and the solution dialyzed and/or ion exchanged to remove the ammonium sulfate and perhaps replace it in whole or in part by sodium chloride.

With all three of these procedures the precipitate which forms is separated, dissolved in distilled water, subjected to a brief dialysis and further treatment.

For the production of the oxygen-free desoxy form the hemoglobin solutions are expediently stirred under vacuum while flushing with nitrogen. The addition of the dialdehydes is effected from aqueous and/or lower alkanol solution, e.g. about 10% concentration, the dialdehyde being added in about 6 to 18 times the molar amount of the hemoglobin. This changes the hemoglobin molecule chemically in such a way that its intravascular residence time is increased while maintaining a low affinity for oxygen so that the oxygen can easily be transferred to the tissue, takes place under conditions of concentration, temperature and pH which produce the desired residence time prolongation and preservation of oxygen bonding capacity and affinity, while effecting almost quantitative reaction. Apparently the reaction achieves prolongation by linkage of the hemoglobin molecule (a) with one or several other hemoglobin molecules,
(b) with serum protein molecules, and
(c) with molecules of gelatin derivatives.

In order to obtain the products according to the invention, there may be used as starting material hemoglobin from humans as well as from various kinds of mammals such as the mouse, rat, rabbit, dog and swine to conduct homologous animal tests and to obtain corresponding animal products. There can be used hemoglobin solutions of about 3 to 20% concentration by weight which solutions may be obtained from the erythrocytes in known manner. Higher hemoglobin concentrations are obtained either by hemolyzing the erythrocytes with the requisite amount of twice distilled water or by concentrating a standard 6% solution by known concentration processes which are carefully conducted so as not to damage the hemoglobin.

For the concentration and the separation of the hemoglobin modified according to the instant invention from hemoglobin which is unmodified or too strongly modified (sparingly soluble), after filtration salting out with ammonium sulfate can be used, to precipitate the desired material, followed by short dialysis and ion exchange through mixed bed exchangers, whereby ammonium and sulfate ions are replaced by sodium and chloride ions, respctively. The hemoglobin solution advantageously contains about 24 to 35 grams of ammonium sulfate, desirably about 26 grams, per 100 ml of solution to effect the salting out.

The drawings show gel chromatographic profiles of various products produced in accordance with the present invention.

The invention will be further described in the following illustrative examples wherein all parts are by weight unless otherwise expressed.

EXAMPLE 1

Coupling together of hemoglobin molecules by way of propanedial (malonic dialdehyde):

Propanedial was generated from the commercial acetalized derivative, malonic dialdehyde-bis(diethyl acetal), by means of 1 N-hydrochloric acid, viz. 1 ml of the acetal was stirred with 2 ml of the acid until clearing of the emulsion, followed by 12-fold dilution with water to produce "Reagent 1."

100 ml of a 3% hemoglobin solution were adjusted with 1 N-soda lye to a pH of 9.0, cooled to 10° to 15° C., magnetically stirred under a vacuum of 20 to 25 mm Hg and washed free of oxygen with nitrogen gas. During constant nitrogen flushing of the gas chamber over the solution, 2 ml of freshly prepared Reagent 1 were added dropwise over one minute. 1 N-soda lye was stirred in simultaneously to maintain the pH at 9.0. Over one hour of stirring the temperature of the reaction mixture increased to 15° to 20° C. After addition of 3 g of glucose and 0.21 g of sodium bicarbonate, the pH was brought to 7.5 by a cation exchanger in the $H^+$-form, the preparation was sterile filtered and refrigerated at 5° C. After three weeks of storage the preparation was characterized gel chromatographically using a modified dextran with three-dimensional cellular structure, sold under the tradename Sephadex by Pharmacia Fine Chemicals of Uppsala, Sweden. The preparation gave the column elution diagram shown in FIG. 1.

In FIG. 1 the course of the height profile (ultraviolet adsorption) from left to right indicates the passage of hemoglobin molecules of descending particle sizes. The peak at G corresponds to hemoglobin which is attached to no other colloid molecules, compared to the shoulder S which indicates higher molecular weight substancs. These higher molecular weight substances are more easily precipitated by ammonium sulfate, i.e., they can be concentrated by a precipitation-fractionation process which is described in detail in Example 2. By means of this precipitation-fractionation there is obtained a preparation which contains a higher content of "double molecules" (molecular weight determination by a membrane osmometer). This concentrated preparation corresponds to a $P_{50}$-value of 15 mm Hg, $P_{50}$ being the oxygen partial pressure required for 50% saturation.

EXAMPLE 2

Coupling of hemoglobin molecules by means of butanedial (succinic dialdehyde):

Butanedial was generated from the commercial cyclic acetal 2,5-diethoxy-tetrahydrofuran similarly to the propanedial of Example 1. The 1:2 mixture of acetal/hydrochloric acid was then, however, diluted 18-fold with water to form "Reagent 2."

Figure 2:
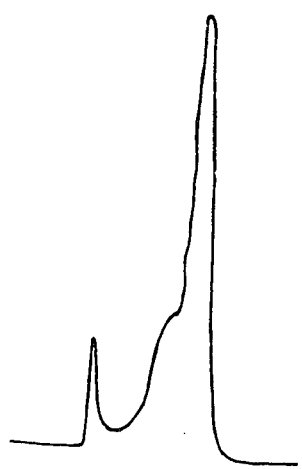

100 ml of an aqueous solution containing 6 g of hemoglobin (acidified to a pH of 6.0 with the $H^+$-form of a cation exchanger) were cooled as in Example 1, rinsed oxygen-free and added to 4 ml of Reagent 2 over two minutes. However, the dropwise addition of soda lye took place only at such rate as to maintain a pH of 6.0. After stirring for one hour at room temperature under a nitrogen atmosphere, the pH value was brought to 7.3–7.5 and the mass processed as in Example 1. After three weeks' refrigerator storage, gel chromatography over Sepharose 6 B (a product sold by Pharmacia Fine Chamicals AB, comprising pearl shaped agarose) indicated a molecular weight distribution as shown in FIG. 2.

Figure 3:
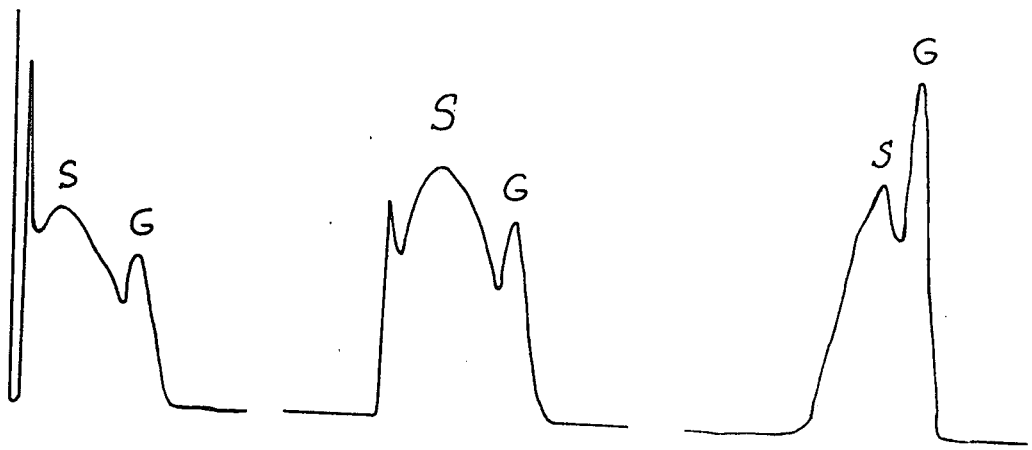

The coupled molecule was concentrated as follows: 4 molar ammonium sulfate solution was dropped into the reaction solution while stirring at room temperature until a stable turbidity resulted. Stirring was continued for 10 minutes, then the formed precipitate was centrifuged off. As shown in FIG. 3, its resolution yielded an accentuated high molecular profile identified as Profile I.

To the clear supernatant was gradually added an equal volume of 4 molar ammonium sulfate solution. The precipitate which formed was isolated and analyzed, producing Profile II, as shown in FIG. 3. The peak S shows preponderance of coupled molecules. Analysis of the supernatant (Profile III) shows the preponderance of uncoupled hemoglobin molecules at peak G.

The $P_{50}$ value of the fraction corresponding to Profile II, of hemoglobin cross-linked with butanedial, was determined as 15.5 mm Hg.

EXAMPLE 3

Figure 4:

Coupling of hemoglobin molecules by means of pentanedial (glutardialdehyde):

100 ml of a solution containing 10 g of hemoglobin at pH 7.5 were reacted with 1.2 ml of 10% pentanedial solution (diluted from 25% aqueous solution of glutardialdehyde) as in Example 1. The preparation was stored for three weeks at 5° C. Gel chromatography produced a profile as in FIG. 4, the material having a $P_{50}$ value of 16.5 mm Hg.

After concentration of the coupled molecule portion corresponding to Profile II, the fractionating salt (ammonium sulfate) was completely removed by dialysis through steam sterilized cellophane tubes at room temperature against 2% sodium chloride solution (magnetic stirring, quadruple change of the 10-fold volume in each case of the dialyzing fluid compared to the preparation within three hours) and through passage through a sterile bed of mixed ion exchangers (100 g each of $Na^+$ and Cl forms respectively). The solution was again sterilized by filtration after being rendered isotonic and being brought to physiological pH. The preparation, which was pyrogen-free, remained in circulation in the blood stream of a rabbit for 5.5 hours (half-time of exchange), having a $P_{50}$ value of 15 mm Hg.

Figure 5:
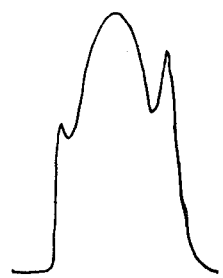

The gel chromatographic profile of the pentanedial coupled hemoglobin, after concentration of the coupled portion, is shown in FIG. 5.

EXAMPLE 4

Coupling of hemoglobin molecules by means of hexanedial (adipic dialdehyde):

Hexanedial was freshly prepared according to K. W. Rosenmund and F. Zetzsche; Chem. Ber. 54, (1921) 2888 from adipic acid dichloride. The waste steam residue which was separated from the solid catalyst and which was still combined with hydrochloric acid was dissolved in a 6-fold volume of ethanol to give "Reagent 4" having a pH of 2-3.

Figure 6:
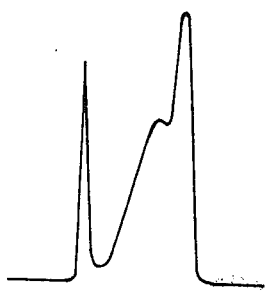

Directly after the production, 4 ml of Reagent 4 were reacted, as in Example 1, with a 14% hemoglobin solution of pH 9. After the same working up and ammonium sulfate fractionation as in Example 2, a gel chromatographic profile was obtained as in FIG. 6, the product having a $P_{50}$ value of 16 mm Hg.

EXAMPLE 5

Figure 7:
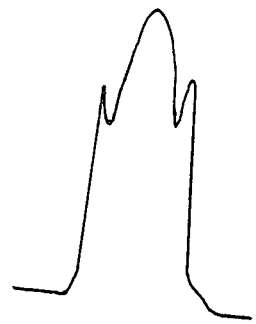

Coupling of hemoglobin molecules by means of octanedial (suberaldehyde):

40 g of suberic acid were boiled in 50 ml of thionyl chloride for two hours under reflux. After another addition of 25 ml thionyl chloride and boiling for an additional three hours under reflux, suberic acid dichloride was distilled off at 143°–145° C. under a pressure of 10 mm Hg. Octanedial was prepared from the suberic acid dichloride according to K. W. Rosenmund and F. Zetzsche, Chem. Ber. 54 (1921) 2888. Each g of the dial was mixed with 10 ml of ethanol to form Reagent 5. 100 ml of a 14% hemoglobin solution of pH 6 were reacted with 4.3 ml of Reagent 5. After suitable processing and concentration of the coupled molecule portion employing ammonium sulfate precipitation, there resulted a preparation which, upon gel chromatography, had the profile shown in FIG. 7, and a $P_{50}$ value of 14.5 mm Hg.

EXAMPLE 6

Figure 8:
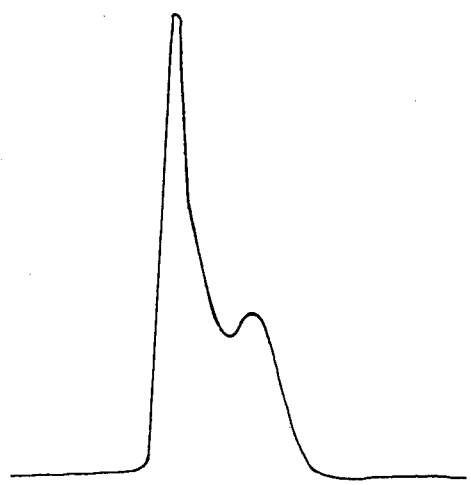

Coupling of hemoglobin to serum albumin:

6.5 g of serum albumin were dissolved in a solution containing 6 g of hemoglobin. This preparation was brought to a pH of 8.5 and further treated according to Example 2, except that 5.1 ml of aqueous butanedial solution (Reagent 2) were added over two minutes and the pH was maintained during two hours of stirring at room temperature. Passage through a cation exchanger in the $H^+$-form brought the pH to 7.3, the product then being sterile filtered and stored under refrigeration. After three weeks, gel chromatography by means of a column of Sephadex G 150 showed a profile as in FIG. 8.

Figure 9:
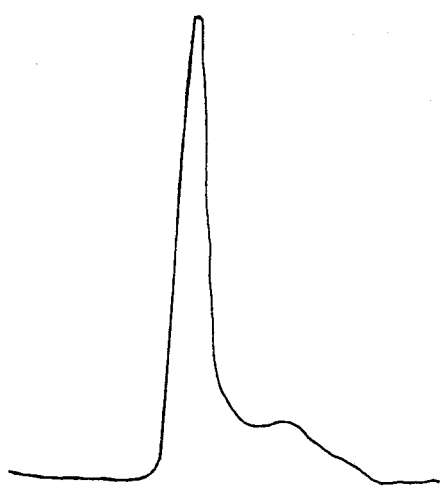

Characterization through foil electrophoresis at a pH of 8.6 showed a strong band for the coupled hemoglobin-albumin between the weaker bands of the slower moving hemoglobin and the faster moving albumin. Through ammonium sulfate fractionation the coupled product was further concentrated and gel chromatography over Sephadex G 150 gave a profile as in FIG. 9, and a $P_{50}$ value of 13 mm Hg.

EXAMPLE 7

Figure 10:
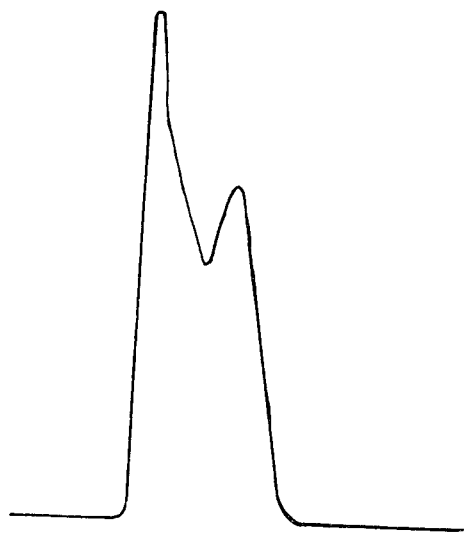

Coupling of hemoglobin to serum albumin:

6.5 g of serum albumin were dissolved in 100 ml of a solution containing 6 g of hemoglobin. This preparation was treated further according to Example 6, with the exception that 1.5 ml of 10% pentanedial solution were added over one minute and the pH, previously adjusted to 9, was maintained during stirring for two hours at room temperature. After three weeks, gel chromatography over a column of Sephadex G 150 produced a profile as in FIG. 10 and $P_{50}$ value of 13.5 mm Hg.

EXAMPLE 8

Coupling of hemoglobin to oxypolygelatin:

A 10% concentrate of oxypolygelatin was added to 100 ml of a 12% hemoglobin solution. This mixture was reacted, according to Example 3, at a pH value of 7.5 with 1.5 ml of 10% pentanedial solution and stored. Gel chromatography over Sephadex G 150 showed the profile of FIG. 11 and a $P_{50}$ value of 15 mm Hg.

EXAMPLE 9

Coupling of hemoglobin to hydrolytically decomposed gelatin:

50 ml of a 6% gelatin preparation (beef bone gelatin which was previously hydrolyzed by heating at a pH of 10 to an average molecular weight ($M_n$) of 25,000) were added to 50 ml of a 6% hemoglobin solution. This mixture was reacted with pentanedial, in accordance with Example 3, at a pH of 7 and with 0.75 ml of the 10% pentanedial solution. After three weeks of storage, the unfractionated end product, further processed as in Example 3, showed a gel chromatographic profile as shown in FIG. 12 and a $P_{50}$ value of 14 mm Hg.

EXAMPLE 10

Coupling of hemoglobin to hydrolytically decomposed gelatin:

50 ml of a decomposed gelatin preparation were mixed with a 6% hemoglobin solution as in Example 9. This mixture was reacted with hexanedial according to Example 4 except that the pH was 7 and there was employed 0.6 ml of the 16% dialdehyde preparation (Reagent 4). The end product, further processed as in Example 4, showed a $P_{50}$ value of 13 mm Hg after ammonium sulfate fractionation.

EXAMPLE 11

Coupling of hemoglobin to serum proteins:

50 ml of a 10% hemoglobin solution were mixed with 50 ml of human serum containing 5% of protein and reacted with pentanedial according to Example 3 except that 1.4 ml of the 10% dialdehyde solution were used and the hemoglobin mixed solution was previously adjusted to a pH of 8.0 The raw product resulting after processing had the profile shown in FIG. 13, and a $P_{50}$ value of 13 mm Hg.

EXAMPLE 12

Coupling of hemoglobin to serum proteins:

50 ml of a 10% hemoglobin solution were mixed with 50 ml of human serum containing 5% of protein and, after adjustment to a pH of 8.0, were reacted analogously to Example 5 with 1.9 ml of octanedial solution. The raw product resulting after processing had a profile as shown in FIG. 14 and a $P_{50}$ value of 13 mm Hg.

EXAMPLE 13

Bonding of pyridoxal phosphate to hemoglobin molecules which are coupled to one another:

To a finished preparation prepared according to Example 1, after three weeks of storage in the refrigerator, there was added 0.1 g of pyridoxal phosphate per 100 ml to lower the oxygen affinity. After an additional three months of storage, the material had a $P_{50}$ value of 17 mm Hg. After gel chromatography over Sephadex G 150, the raw product had the profile shown in FIG. 15.

EXAMPLE 14

Figure 16:
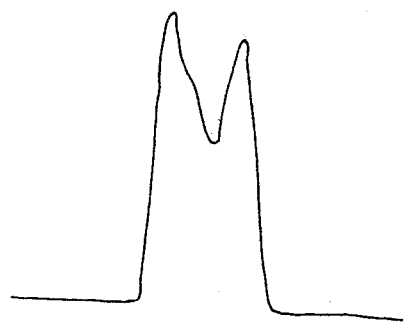

Bonding of pyridoxal phosphate to coupled hemoglobin molecules:

After 3 weeks of storage in the refrigerator, to a raw product prepared in accordance with Example 3, there was added 0.1 g of pyridoxal phosphate per 100 ml. A $P_{50}$ value of 16.5 mm Hg was measured for the preparation. After gel chromatography over Sephadex G 150 it showed the profile illustrated in FIG. 16.

EXAMPLE 15

Figure 17:

Under a nitrogen atmosphere, 100 ml of a 4 molar $(NH_4)_2SO_4$ solution were gradually stirred into 100 ml of solution at pH 7.5 containing 12 g of hemoglobin. Then 2.4 ml of 10% pentanedial solution were dropped in followed by stirring for half an hour. After centrifugal the precipitate was dissolved in distilled water. The $P_{50}$ value was 14 mm Hg. It had a gel chromatographic profile as in FIG. 17.

EXAMPLE 16

Figure 18:

90 ml of 4 molar ammonium sulfate solution containing 4 ml of hexanedial (Reagent 4) were added slowly to 100 ml of a 14% hemoglobin solution. After stirring for half an hour under nitrogen, the precipitate was separated by centrifugation and dissolved in distilled water. The resulting solution had a $P_{50}$ value of 14 mm Hg and showed the gel chromatographic profile of FIG. 18.

Animal tests showed the products to be pyrogen-free and antigen-free. In vivo and in vitro tests showed the products to be comparable in oxygen supply capacity with free hemoglobin, and better in residence time. Specifically, by the test method of K. Bonhard in Anaesthetist 23 (1974) 78–82, in rabbits there were measured the half-life periods of the intravascular residence time after replacement of blood with 15 ml per Kg of body weight of various hemoglobin preparations containing 6 g of hemoglobin per 100 ml. Compared with a residence time of 2 to 3 hours for untreated hemoglobin, the novel preparations showed residence times of as much as 5 to 10 hours. Specific trial results are shown in Table 1:

TABLE 1

| Preparation | Time in hours Crude products | high molecular fraction gel chromate/Sephadex G 150 |
| --- | --- | --- |
| Unmodified hemoglobin | 2 | — |
| Dialdehyde-cross-linked hemoglobin (as in Examples 1–5, 13 and 14) | 4.3 | 9 |
| Hemoglobin coupled to albumin (as in Examples 6, 7, 11 and 12) | 8.3 | |
| Hemoglobin coupled to gelatin (as in Examples | | |

TABLE 1-continued

| Preparation | Time in hours Crude products | high molecular fraction gel chromate/Sephadex G 150 |
|---|---|---|
| 8-10) | 4 | |

In Table 2 there are shown further characteristics of the products:

TABLE 2

| Preparation | $O_2$—capacity | (% of theory)[1] | $P_{50}$[2] |
|---|---|---|---|
| Unmodified hemoglobin (Comparison) | | 80 | 21-23 |
| Dialdehyde cross-linked hemoglobin (Examples 1-5, 13 and 14) | Crude product: | 75 | 18 |
| | Concentrated fraction of Example 1 | 65 | 15 |
| Hemoglobin bonded to albumin (Examples 6, 7, 11 and 12) | Crude product: | 70 | |
| | Concentrated fraction of Example 6: | 70 | 13 |
| Hemoglobin bonded to gelatin (Examples 8-10) | Crude product: | 75 | 15 |
| | Concentrated fraction of Example 10 | 70 | 13 |

[1]Capacity for binding oxygen (percentage of the theoretical $O_2$ bond of completely untreated hemoglobin),
[2]$P_{50}$ values at 37° C., pH 7.45

It will be appreciated that the instant specification and claims are set forth by way of illustration and not limitation, and that various modifications and changes may be made without departing from the spirit and scope of the present invention:

What is claimed is:

1. A chemically modified, stable hemoglobin preparation suitable for blood replacement and for organ perfusion, comprising hemoglobin molecules coupled to one another or to another protein selected from the group consisting of serum proteins and gelatin derivatives by a coupling reagent comprising an aliphatic dialdehyde having 3 to 8 carbon atoms, molar ratio of the coupling reagent to the hemoglobin being about 6:1 to about 18:1, the preparation having a capacity to transport oxygen corresponding approximately to that of free hemoglobin, and a blood residence time which is at least about twice that of free hemoglobin.

2. A process for producing a hemoglobin preparation according to claim 1, comprising adding to substantially oxygen-free hemoglobin the dialdehyde coupling reagent in a molar ratio of the dialdehyde to the hemoglobin of about 6:1 to about 18:1 and isolating the coupled hemoglobin.

3. The process of claim 2 comprising adding pyridoxal phosphate to the reaction mixture of the hemoglobin and the dialdehyde and wherein, after the pyridoxal phosphate has been added, the coupled hemoglobin is isolated as a precipitate by salting out with ammonium sulfate and, then, the ammonium sulfate in the product is partly replaced with sodium chloride.

4. The process of claim 2 wherein the dialdehyde is added as a solution in at least one of water and a lower alkanol.

5. The process of claim 4 wherein the aldehyde is added to and mixed with the hemoglobin under a nitrogen atmosphere.

6. The process of claim 2 wherein the coupled hemoglobin is isolated as a precipitate by salting out with ammonium sulfate.

7. The process of claim 6 wherein the ammonium sulfate is present in the hemoglobin prior to coupling.

8. The process of claim 4 wherein ammonium sulfate is added to the hemoglobin with the dialdehyde.

9. The process of claim 6 wherein the ammonium sulfate is added to the hemoglobin preparation after coupling.

10. The process of claim 6 including the further steps of dissolving the precipitate, and removing ammonium sulfate therefrom.

11. The process of claim 1 wherein serum albumin momlecules are present along with the hemoglobin molecules and are coupled to the hemoglobin molecules.

12. The process of claim 2 wherein gelatin derivative molecules are present along with the hemoglobin molecules and are coupled to the hemoglobin molecules.

* * * * *